United States Patent [19]

Seig

[11] Patent Number: 4,482,758

[45] Date of Patent: Nov. 13, 1984

[54] PROCESS FOR THE ORTHOMETHYLATION OF PHENOLIC COMPOUNDS

[75] Inventor: Reinhard Seig, Marl, Fed. Rep. of Germany

[73] Assignee: Chemische Werke Huels AG, Marl, Fed. Rep. of Germany

[21] Appl. No.: 449,294

[22] Filed: Dec. 13, 1982

[30] Foreign Application Priority Data

Dec. 11, 1981 [DE] Fed. Rep. of Germany ....... 3149022

[51] Int. Cl.$^3$ ............................................. C07C 37/16
[52] U.S. Cl. .................................... 568/804; 568/780
[58] Field of Search ................ 568/804, 794, 789, 780

[56] References Cited

FOREIGN PATENT DOCUMENTS

| 739786 | 3/1970 | Belgium | 568/804 |
| 851227 | 9/1970 | Canada | 568/804 |
| 0050937 | 10/1981 | European Pat. Off. | 568/804 |
| 1297110 | 6/1969 | Fed. Rep. of Germany | 568/804 |
| 50-49236 | 5/1975 | Japan | 568/804 |
| 51-12610 | 4/1976 | Japan | 568/804 |
| 51-42092 | 11/1976 | Japan | 568/804 |
| 717588 | 10/1954 | United Kingdom | 568/804 |
| 1124839 | 8/1968 | United Kingdom | 568/804 |
| 1323211 | 7/1973 | United Kingdom | 568/804 |
| 1428057 | 3/1976 | United Kingdom | 568/804 |
| 1507478 | 4/1978 | United Kingdom | 568/804 |
| 2072674A | 10/1981 | United Kingdom | 568/804 |

Primary Examiner—Werren B. Lone
Attorney, Agent, or Firm—Millen & White

[57] ABSTRACT

For the orthomethylation of phenolic compounds containing at least one hydrogen atom in the ortho position, the phenol compound is reacted with methanol in the gaseous phase in the presence of an oxidic catalyst containing iron, chromium, and cerium in an atomic ratio of Fe:Cr:Ce of 1:0.005 to 0.1:0.005 to 0.1, at temperatures of 270°–450° C., pressures of 1–40 bar, and rates per unit volume of 0.05–3 h$^{-1}$. The temperature within the catalyst bed is maintained constant within a narrow temperature range $\Delta T$ of up to 20° C. The catalyst has a very long service life with a high activity, and provides a high selectivity.

14 Claims, No Drawings

PROCESS FOR THE ORTHOMETHYLATION OF PHENOLIC COMPOUNDS

BACKGROUND OF THE INVENTION

The present invention relates to a process for the gas phase selective orthomethylation of phenols having at least one hydrogen atom in the ortho position.

It is known from DAS No. 2,127,083 (=British Pat. No. 1,323,211) that methanol can be reacted with phenols of the mentioned general structure on a catalyst containing manganese oxide and cerium oxide at temperatures of 300°–550° C. British Pat. No. 717,588 discloses that methanol reacts with o-cresol in the gaseous phase in the presence of a catalyst made up of only one of the following metallic oxides: oxides of magnesium, aluminum, calcium, manganese, iron, zinc, zirconium, barium, or thorium. British Pat. No. 1,124,839 describes a process for the production of alkyl phenols wherein a phenol is reacted with an alcohol in the presence of an oxide of a rare earth element, such as, for example, cerium, lanthanum, neodymium, and praseodymium. All of the catalysts utilized in these processes contain only one of the active components, iron oxide or cerium oxide.

These conventional catalysts exhibit several disadvantages. They have low activity and low selectivity for the orthoalkylation. Additionally, they result in a high loss of methanol. Also, the lifetime of these catalysts is short.

Furthermore, catalysts comprised of iron oxide and silicic acid (hydrated silica) or of iron oxide, silicic acid, and chromium oxide have been suggested for the preparation or orthoalkyl phenols with high selectivity (DAS No. 2,428,056=British Pat. No. 1,428,057). However, the binary catalyst also exhibits a strong reduction in activity during a prolonged operating period. The ternary catalyst, on the other hand, does have a longer lifetime compared with the binary catalyst. Moreover, this can be still further improved by using a quaternary catalyst consisting of iron oxide, silicic acid, chromium oxide, and an alkali metal compound or alkaline earth metal compound (German Pat. No. 2,547,309=British Pat. No. 1,507,478 and Belgian Pat. No. 888,022=British Pat. No. 2,072,674). However, such lifetimes are still inadequate for industrial utilization.

SUMMARY OF THE INVENTION

Accordingly, it is an object of this invention to provide an industrially usable catalyst, fulfilling the important requirements of high selectivity and yield with a considerably improved service life.

It is another object of this invention to provide a gaseous phase catalytic process for the orthomethylation of phenol compounds having at least one hydrogen atom in the ortho position, which process can be performed in a simple way and on an industrial scale while simultaneously improving activity, selectivity, yield, and service life of the catalyst.

Upon further study of the specification and appended claims, further objects and advantages of this invention will become apparent to those skilled in the art.

These objects have been achieved by providing a process for the orthomethylation of phenolic compounds having at least one hydrogen atom in the ortho position therewith, by reaction in the gaseous phase with methanol in a molar ratio of phenol compound to methanol of 1:1 to 1:10 in the presence of a metal oxide catalyst at temperatures of 270°–450° C., under a pressure of 1–40 bar absolute, and with rates per unit volume (LHSV) of 0.05–3 $h^{-1}$ to obtain o-cresol, 2,6-dimethylphenol, 2,3- or 2,4-dimethylphenol and/or 2,3,6- or 2,4,6-trimethylphenol, wherein the metallic oxide catalyst comprises a calcined mixture of the oxides of iron, chromium, and cerium in an atomic ratio of Fe:Cr:Ce of 1:0.005 to 0.1:0.005 to 0.1 respectively, and wherein the temperature within the catalyst bed is maintained substantially constant within a temperature range of up to 20° C.

DETAILED DISCUSSION

The ternary catalyst of this invention, which contains the calcined ternary oxidic mixture of iron oxide ($Fe_2O_3$, $Fe_3O_4$), chromium oxide ($Cr_2O_3$), and cerium oxide ($Ce_2O_3$) in the mentioned molar ratios, surprisingly, is catalytically active for a substantially longer period of time in comparison with the conventional catalysts, and even in comparison with the known quaternary catalysts. The ternary catalyst used in accordance with this invention shows an especially high selectivity in the direction of formation of 2,6-dimethylphenol and o-cresol, as well as providing a surprisingly high ratio of the yield of 2,6-dimethylphenol to o-cresol. In this connection, it is an especially significant advantage that the catalyst retains its high activity and selectivity over a time period of 3,000 hours and more. Within the catalyst bed, the temperature is kept extensively constant in a narrow temperature range ($\Delta T$) of up to 20° C., preferably up to 8° C., especially up to 5° C., the temperature being within the mentioned range of 270°–450° C., of course, i.e., the reaction temperature variation is $\pm\frac{1}{2} \Delta T$ ($\pm 10°$ C., $\pm 4°$ C., $\pm 2.5°$ C.) centered about a temperature of 270°–450° C.

Examples of suitable starting material phenol compounds include phenol, o-cresol, p-cresol, and m-cresol. Any phenolic compound having at least one H-atom in an ortho position and up to three alkyl substitents in any combination of positions.

The phenol compounds are reacted with methanol in a molar ratio of phenol:methanol of 1:1 to 1:10, preferably 1:2 to 1:10, especially 1:3 to 1:6.

The process of this invention is primarily directed to the reaction with methanol; however, similarly improved results will be achieved using other alcohols, especially lower alcohols.

The methylation takes place in the gaseous phase at temperatures of 270°–450° C., preferably 290°–350° C. under a pressure of 1–40 bar absolute, preferably 3–30 bar absolute, the lower pressure range being employed in the lower temperature range.

The reaction mixture can be diluted with inert gases, such as nitrogen, so that the partial pressure of the mixture of phenol compound and methanol can also be below 1 bar absolute. The reaction takes place at rates per unit volume (LHSV, i.e., liters feed stream per hour per volume of catalyst (liters), based on the liquid feed components, of 0.05 $h^{-1}$ to 3 $h^{-1}$, preferably 0.08 $h^{-1}$ to 1 $h^{-1}$.

If a phenol with 2 hydrogen atoms in the ortho position is alkylated with methanol, it is possible to produce the corresponding dimethylated phenol as well as the monomethylated phenol. Practically no non-phenolic by-products are formed in this reaction. In addition to participating in the alkylation, methanol can also engage in a decomposition reaction on the catalyst primarily to form carbon monoxide and hydrogen. These decomposition products continue to react extensively to $CO_2$, $CH_4$, and $H_2O$.

By a selection of suitable reaction conditions, the process can be regulated so that it leads predominantly to the formation of a dimethylated phenol or predominantly to the formation of the monomethylated phenol. Selection in this regard can be accomplished routinely based on conventional considerations with reference to the details of this application. In this way, the yield and selectivity of phenols dimethylated in the ortho position can be considerably increased when starting with phenols having two hydrogen atoms in the ortho positions, e.g., by raising the ratio of methanol to phenol used in the inlet feed stream by increasing the reaction temperature, by elevating the reaction pressure, or by lowering the rate per unit volume. By changing these parameters in an opposite direction, phenols are obtained which are preferably monomethylated in the ortho position. Thus, the catalyst of this invention provides a high selectivity and a high yield in the direction of orthoalkylation, and a high ratio of double-orthoalkylation to mono-othoalkylation (if desired) for extended periods of time.

For example, for the preparation of o-cresol, the starting phenolic compound and the methanol are preferably reacted in molar ratios of 1:1 to 3 at temperatures of 270°–350° C., pressures of 1–4 bar, and with a rate per unit volume LHSV of 0.05–3 $h^{-1}$. For producing 2,6-dimethylphenol, the process is preferably conducted at a rate per unit volume LHSV of 0.08–1 $h^{-1}$, molar ratios of phenol compound to methanol of 1:3 to 6, temperatures of 300°–450° C., and pressures of 3–30 bar.

Any conventional reactor useful for conducting reactions in the gaseous phase can be employed in conducting the process of this invention. Advantageous are reactors wherein the exothermic heat of the entire reaction is very efficiently removed, and wherein a maximally uniform internal reactor temperature can be maintained over the whole length of the catalyst bed, whereby the temperature difference of up to 20° C., preferably up to 8° C., especially up to 5° C. can be readily obtained over the catalyst bed. This can be accomplished, for example, by using a conventional multiple-tube reactor with satisfactory heat removal and a small inner tube diameter, advantageously of up to 50 mm, or by conventionally diluting the catalyst with catalytically inert material, or by diluting the reactants with inert gaseous components, i.e., diluting the educt from the mixing operation of the two reactants. Suitable such catalytically inert materials include, for example, ceramic, glass elements, or corundum. The inert material is utilized in amounts of 1–30% by weight, based on the amount of active catalyst. Examples of suitable inert gaseous components which can be used are nitrogen, e.g., in amounts of 0.1–10 parts by volume per part by volume of gaseous feed.

The process can be conducted, for example, by feeding a phenol, having at least one hydrogen atom in the ortho position, and methanol separately or in a mixture, diluted or in pure form, into a preheater in communication with a reactor, advantageously having the aforedescribed design. In this reactor, the catalyst is provided in dilute or pure form. Thereby, the vaporized and preheated reactants are continuously placed into contact with the catalyst bed in the pure form or with an inert carrier gas such as nitrogen.

The cataylst bed is optionally heated from the outside. The internal reactor temperature is maintained maximally constant over the entire catalyst bed, e.g., by the aforedescribed steps. By this measure, as well as by the choice of the catalyst composition of this invention, an increased selectivity of the formation of, for example, 2,6-dimethylphenol or selectively o-cresol is obtained. Simultaneously, the methanol decomposition is considerably decreased. The gaseous reaction products formed in the reactor are then liquefied in a separator. The liquefied reaction products contain high proportions of orthomethylated products of phenol and can be obtained in the pure form by various purification methods known per se, such as, for example, by distillation, extraction, recrystallization. The optimum reaction temperature depends on the o-methylation product of phenol to be produced in a particular case, on the rate per unit volume selected, on the pressure selected, and on the composition of the catalyst. Precisely favorable combinations can be routinely determined by conventional considerations in view of this application, perhaps with a few routine preliminary experiments. These temperatures range from 270° to 450° C., preferably from 290° to 350° C. The rate per unit volume, based on the liquid feed components, can be varied in a range of LHSV=0.05 $h^{-1}$ to 3 $h^{-1}$, preferably in a range of LHSV=0.08 $h^{-1}$ to 1 $h^{-1}$. The pressure can be chosen within a wide range from 1 bar to 40 bar absolute.

Preferably, the reaction is conducted under a pressure of 3–30 atmospheres. In such cases, the process can be conducted at an increased rate per unit volume, and the decomposition of methanol primarily into carbon monoxide and hydrogen, as well as the further reaction of these decomposition products, is reduced. The temperature in the vaporizer is uncritical per se; but it is advantageous to lower the evaporation temperature of the phenols by passing methanol in vapor phase through the phenol solution, or by initially vaporizing a mixture of phenol with methanol.

The molar ratio of methanol to the corresponding feed phenols can be varied, depending on whether the feed phenol has one or two hydrogen atoms in the ortho position, and depending on whether the desired product is to be mono- or dimethylated in the ortho position, as discussed above. The molar ratio in the reactant mixture ranges from 1 to 10 moles of methanol per mole of phenolic compound, preferably 2–10 moles, especially 3–6 moles per mole of phenolic compound. Unreacted methanol and/or phenolic compounds can be readmixed to the reactant streams after separation from the reaction product.

The catalyst of this invention consists essentially of a calcined mixture of iron oxide, chromium oxide, and cerium oxide in an atomic ratio of Fe:Cr:Ce of 1:0.005 to 0.1:0.005 to 0.1, preferably 1:0.005 to 0.02:0.005 to 0.02. Catalysts suitable for use in this invention can be manufactured, for example, according to conventional methods, as a precipitated catalyst or by intimate mixing of the oxides of iron (e.g., $Fe_2O_3$), chromium ($Cr_2O_3$), and cerium ($Ce_2O_3$), or by a combination of both methods, or by impregnating $Fe_2O_3$ with chromium and cerium (G. M. Schwab, Handbuch der Katalyse (1934). whose disclosures are incorporated by reference herein. The precipitation process is especially preferred among the above-recited methods.

For example, an aqueous solution of the nitrates, chlorides, or sulfates of trivalent iron, chromium, and cerium can be precipitated with an alkaline medium; the supernatant solution can be filtered off, and the washed precipitate can be dried. The dried precipitate, prepared by such a method or any other conventional method, can then be molded into a shape, such as, e.g., tablets, pellets, or extruded forms, and then calcined for 5–10 hours at 300°–500° C. The atomic ratio of iron to chromium to cerium is 1:0.005 to 0.1:0.005 to 0.1.

The products of phenol, methylated in the ortho position according to the process of this invention, can be used for all the purposes of such products in the prior art, e.g., as starting materials for the synthesis of herbicides, antioxidants, antiseptics, vitamin E, etc., Ullmanns Encyklopädie der technischen Chemie, 4. ed. vol. 15, p. 75; 3. ed., 13 vol., page 446, whose disclosures are incorporated by reference herein. 2,6-Dimethylphenol is utilized, in particular, as the starting compound for producing polyphenylene oxide. They are also useful as conventional solvents for conducting many reactions, and can be used conventionally to prepare another of the products produced by this invention (Ullmanns Encyklopädie der technischen Chemie, 4. ed., vol. 15, page 75).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

COMPARATIVE EXAMPLE 1

For the production of the catalyst, 300 g of iron(III) nitrate is dissolved in 3 l of distilled water. First, 1.6 g of sodium silicate is added to the solution, then the trivalent iron is completely precipitated from the solution while stirring with a 10% ammonia solution. After washing with water and drying of the filtered precipitate, the catalyst powder is aftertreated at room temperature in dilute aqueous potassium carbonate solution. The precipitate, after having been filtered once more and dried, is compressed into tablets and calcined for 7 hours at 470° C. The weight of the catalyst batch is 43 g. A reactor having an inner diameter of 22 mm is charged with 33.2 g of the catalyst; the temperature is controlled by a saline bath. By means of a continuously operated liquid metering pump, a methanol/phenol mixture with a molar ratio of 5/1 moles methanol/mole phenol and a rate per unit volume of LHSV = 0.68 $h^{-1}$, is vaporized in a vaporizer at 140° C. and preheated to 300° C. Nitrogen is added to the gaseous mixture as the carrier gas before entrance into the reactor. The exactly set nitrogen content serves simultaneously as an inner standard for the gas-chromatographic analysis of the decomposition products of methanol. At a reaction temperature of 337° C., a phenol conversion is obtained of 95% with a 57% yield of 2,6-dimethylphenol and a 35% yield of o-cresol. These yields can be obtained only within a time period of 50 hours. Subsequently, activity and selectivity of the formation of 2,6-dimethylphenol drop greatly. In addition, small amounts of anisole, 2,5-dimethyl-phenol, 3,6-dimethylphenol, and 2,4-dimethylphenol are detected. The methanol decomposition yields 24 mmol/h of $CO_2$, 15 mmol/h of $CH_4$, 5 mmol/h of CO. Furthermore, hydrogen is formed.

COMPARATIVE EXAMPLE 2

300 g of iron(III) nitrate and 3 g of chromium(III) nitrate are dissolved in 3 l of distilled water and then the iron and chromium are completely precipitated from the solution under continuous agitation with 10% ammonia solution. After washing with water and drying of the filtered precipitate, the catalyst powder is aftertreated in dilute aqueous potassium carbonate solution. The precipitate, which is once more filtered and dried, is compressed into tablets and calcined for 7 hours at 470° C. The catalyst has an atomic ratio of iron to chromium of 1:0.01.

29.5 g of the catalyst is charged with a 5/1 moles methanol/mole phenol mixture with LHSV of 0.68 $h^{-1}$. The gaseous mixture, diluted with $N_2$ as the carrier gas after its vaporization at 140° C., is converted to an extent of 83% at 372° C. The yield is 34% of 2,6-dimethylphenol and 47% of o-cresol. After an operating period of 40 hours, the catalyst activity and selectivity decrease sharply.

COMPARATIVE EXAMPLES 3–6

300 g of iron(III) nitrate, 3 g of chromium(III) nitrate, and 1.6 g of sodium silicate, dissolved in 3 l of distilled water, are precipitated with 10% ammonia solution, washed, filtered, dried at 180° C., compressed into tablets, and calcined in an air stream for 7 hours at 470° C. The catalyst, containing iron, chromium, and silicon in an atomic ratio of 1:0.01:0.01, yields the following results in the methylation of 5:1 moles methanol/mole phenol mixture passed into the reactor after vaporization at 140° C. with $N_2$ as the carrier gas:

| No. | LHSV $h^{-1}$ | ΔT °C. | T Reactor °C. | Conversion Phenol % | Yield o-Cresol % | Yield 2,6-DMP % | Selectivity 2,6-DMP % |
|---|---|---|---|---|---|---|---|
| 3 | 0.68 | 12 | 325 | 90 | 55 | 33 | 39 |
| 4 | 0.47 | 15 | 334 | 94 | 50 | 42 | 46 |
| 5 | 0.47 | 15 | 327 | 92 | 36 | 48 | 52 |
| 6 | 0.47 | 18 | 350 | >99 | 4 | 90 | 90 |

After an operating period of 400 hours, the activity and selectivity of the catalyst diminish greatly.

EXAMPLES 7 AND 8

900 g of iron(III) nitrate, 4.5 g of chromium(III) nitrate, and 4.8 g of cerium(III) nitrate are dissolved in 9 l of distilled water and precipitated with 10% ammonia solution, then washed, filtered, dried at 170° C., compressed into tablets, and calcined in an air stream for 7 hours at 470° C. The catalyst has an atomic ratio of Fe:Cr:Ce of 1:0.005:0.005.

The results set out below are obtained in the methylation of a 5:1 mole methanol/mole phenol mixture passed into the reactor after vaporization at 220° C.:

| No. | LHSV $h^{-1}$ | T React. °C. | ΔT °C. | Conversion Phenol % | Yield o-Cresol % | Yield 2,6-DMP % |
|---|---|---|---|---|---|---|
| 7 | 0.13 | 314 | 4 | >99 | 11 | 86 |
| 8,1 | 0.08 | 316 | 4 | >99 | 4 | 94 |
| 8,2 | 0.08 | 317.5 | 5 | >99 | 8 | 90 |
| 8,3 | 0.08 | 318 | 5 | >99 | 6.5 | 91 |
| 8,4 | 0.08 | 318.5 | 2.5 | >99 | 8.2 | 89.5 |
| 8,5 | 0.08 | 320 | 3 | >99 | 0.3 | 96.4 |

-continued

| No | CH₃OH Loss by Decomposition to $CO_2$, $CH_4$, CO and $H_2$ % | Operating Period h |
| --- | --- | --- |
| 7 | 24 | 120 |
| 8,1 | 25.5 | 860 |
| 8,2 | 27.1 | 1,340 |
| 8,3 | 30 | 1,500 |
| 8,4 | 30 | 2,000 |
| 8,5 | 33 | 3,000 |

Conversion and yield remain practically constant within the operating period under investigation.

EXAMPLES 9–16

1.8 kg of iron(III) nitrate, 18 g of chromium(III) nitrate, and 19.3 g of cerium(III) nitrate, dissolved in 18 l of water, are precipitated with 10% ammonia solution, filtered, washed, dried at 170° C., compressed into pills, and tempered in an air stream at 470° C. for 7 hours. The atomic ratio of Fe:Cr:Ce in the catalyst is 1:0.01:0.01.

The following results are obtained when methylating with a 6:1 mole methanol/mole phenol mixture:

| No. | LHSV h⁻¹ | T React. °C. | ΔT °C. | $P_E$* bar | Conversion Phenol % | Yield o-Cresol % | Yield 2,6-DMP % | Operating Period h |
| --- | --- | --- | --- | --- | --- | --- | --- | --- |
| 9 | 0.37 | 376 | 12 | 3.3 | 94 | 53 | 36 | 280 |
|  | 0.37 | 380 | 12 | 3.3 | 92 | 59 | 32 | 550 |
| 10 | 0.37 | 377 | 12 | 4.4 | 94 | 53 | 38 | 600 |
| 11 | 0.37 | 380 | 13 | 5.5 | 95 | 45 | 46 | 700 |
| 12 | 0.24 | 380 | 13 | 1.7 | 89 | 60 | 26 | 1000 |
| 13 | 0.24 | 380 | 13 | 10 | 90 | 40 | 46 | 750 |
| 14 | 0.24 | 380 | 12 | 30 | 95 | 33 | 59 | 750 |
| 15 | 0.24 | 380 | 8 | 30 | 90 | 31 | 55 | 1500 |
| 16 | 0.24 | 400 | 8 | 35 | 90 | 25 | 61 | 3000 |

*excess

Conversion and yield remain practically constant during the trial operating period.

The same results are obtained by using a catalyst containing 10% by weight of glass beads having a diameter of 2–4 mm, based on the catalyst utilized in this example.

EXAMPLE 17

43 g of the catalyst from Examples 7 and 8 is filled into a reactor having an inner diameter of 22 mm; temperature control is executed by a saline bath. An o-cresol/methanol mixture with a molar ratio of 3 moles methanol/1 mole o-cresol is reacted at a rate per unit volume of LHSV=0.5 h⁻¹ and an internal reactor temperature of 335° C. (ΔT 8° C.) under 3 bar. The o-cresol conversion is >99%, the yield of 2,6-dimethylphenol amounts to 98%.

EXAMPLE 18

43 g of the catalyst from Examples 7 and 8 is used in accordance with the description of Example 17, but with a p-cresol/methanol mixture having a molar ratio of 5 moles methanol/1 mole p-cresol. With a practically complete conversion of p-cresol (>99%), the yield of 2,4-dimethylphenol is 36% and the yield of 2,4,6-trimethylphenol is 59%.

EXAMPLE 19

43 g of the catalyst according to Example 17 is used according to the description of that example but with an m-cresol/methanol mixture of a molar ratio of 5 moles methanol/1 mole m-cresol.

Conversion (m-cresol) >99%.
Yield (2,3-dimethylphenol) =45%.
Yield (2,3,6-trimethylphenol) =46%.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the orthomethylation of a phenolic compound having at least one hydrogen atom in an ortho position, comprising reacting the phenolic compound with methanol, in the gaseous phase, in a molar ratio of phenolic compound to methanol of from 1:1 to 1:10, at a temperature of 270°–450° C., under a pressure of 1–40 bar absolute, at a flow rate per unit volume (LHSV) of 0.05–3 h⁻¹, using a catalytically effective amount of a metallic oxide catalyst comprising a calcined mixture of the oxides of iron, chromium, and cerium in an atomic ratio of Fe:Cr:Ce of 1:0.005 to 0.1:0.005 to 0.1, and maintaining said reaction temperature substantially constant within a temperature range of up to 20° C., to produce o-cresol, 2,6-dimethylphenol, 2,3- or 2,4-dimethylphenol and/or 2,3,6- or 2,4,6-trimethylphenol.

2. A process of claim 1, wherein the metallic oxide catalyst contains iron, chromium, and cerium in an atomic ratio of 1:0.005 to 0.02:0.005 to 0.02.

3. A process of claim 1, wherein the reaction is conducted over a catalyst bed containing the metal oxide catalyst, and the temperature within the catalyst bed is maintained substantially constant within a range of up to 8° C.

4. A process of claim 1, wherein the reaction is conducted over a catalyst bed containing the metal oxide catalyst, and the temperature within the catalyst bed is maintained substantially constant within a range of up to 5° C.

5. A process of claim 2, wherein the reaction is conducted over a catalyst bed containing the metal oxide catalyst, and the temperature within the catalyst bed is maintained substantially constant within a range of up to 8° C.

6. A process of claim 1, wherein the phenolic compound is phenol, or o-, m- or p-cresol.

7. A process of claim 1, wherein the molar ratio of phenol to methanol is 1:3 to 1:6.

8. A process of claim 1, wherein the reaction temperature is 290°–350° C., the reaction pressure is 3–30 bar absolute, and the flow rate is 0.08 to 1 h⁻¹ (LHSV).

9. A process of claim 1, wherein the catalyst has been calcined at 300°–500° C. for 5–10 hours.

10. A process of claim 1 which is conducted using values in the higher portion of said phenol to methanol ratio range, the higher portion of said temperature range, the higher portion of said pressure range and the lower portion of said flow rate range, thereby increasing the selectivity of the process for producing phenols dimethylated in the ortho positions.

11. A process of claim 1 which is conducted using values in the lower portion of said phenol to methanol ratio range, the lower portion of said temperature range, the lower portion of said pressure range and the higher portion of said flow rate range, thereby increasing the selectivity of the process for producing phenols monomethylated in the ortho position.

12. A process of claim 11 conducted with a rate per unit volume LHSV of 0.5–3 $h^{-1}$, a molar ratio of phenol to methanol of 1:1 to 3, a temperature of 270°–350° C., and a pressure of 1–4 bar, to increase the selectivity of production of o-cresol.

13. A process of claim 10 conducted with a rate per unit volume LHSV of 0.05–1 $h^{-1}$, a molar ratio of phenolic compound to methanol of 1:3 to 6, a temperature of 300°–450° C., and a pressure of 3–30 bar, to increase the selectivity of production of 2,6-dimethylphenol.

14. A metallic oxide catalyst comprising a calcined mixture of the oxides of iron, chromium, and cerium in an atomic ratio of Fe:Cr:Ce of 1:0.005 to 0.1:0.005 to 0.1.

* * * * *